US012268800B2

(12) United States Patent
Spittler et al.

(10) Patent No.: US 12,268,800 B2
(45) Date of Patent: Apr. 8, 2025

(54) FLUID-FLOW STERILIZATION ENGINE AND METHOD FOR USING THE SAME

(71) Applicant: PH LABS, LLC, Mentor, OH (US)

(72) Inventors: Michael John Spittler, Mentor, OH (US); John Bowles, Mentor, OH (US)

( * ) Notice: Subject to any disclaimer, the term of this patent is extended or adjusted under 35 U.S.C. 154(b) by 0 days.

(21) Appl. No.: 18/923,445

(22) Filed: Oct. 22, 2024

(65) Prior Publication Data

US 2025/0041472 A1 Feb. 6, 2025

Related U.S. Application Data

(62) Division of application No. 17/405,367, filed on Aug. 18, 2021.

(60) Provisional application No. 63/070,517, filed on Aug. 26, 2020, provisional application No. 63/068,151, filed on Aug. 20, 2020, provisional application No. 63/067,239, filed on Aug. 18, 2020.

(51) Int. Cl.
*A61L 9/20* (2006.01)
*C02F 1/32* (2023.01)

(52) U.S. Cl.
CPC ............. *A61L 9/20* (2013.01); *A61L 2209/14* (2013.01); *C02F 1/32* (2013.01); *C02F 2201/3222* (2013.01); *C02F 2201/3228* (2013.01); *C02F 2303/04* (2013.01)

(58) Field of Classification Search
CPC .......... A61L 9/20; A61L 2209/14; C02F 1/32; C02F 2201/3222
See application file for complete search history.

(56) References Cited

U.S. PATENT DOCUMENTS 5,019,256 A * 5/1991 Ifill .......................... C02F 1/325 210/243
2015/0284265 A1* 10/2015 Borkar .................... C02F 1/325 210/192

FOREIGN PATENT DOCUMENTS

CN 203959876 U * 11/2014

OTHER PUBLICATIONS

English translation of CN203959876U (Year: 2014).*

* cited by examiner

*Primary Examiner* — Sean E Conley
(74) *Attorney, Agent, or Firm* — Quarles & Brady LLP; Yakov S. Sidorin

(57) ABSTRACT

Efficient sterilization of a flow of fluid containing a pathogen/virus contaminant is achieved by filtering the fluid while exposing the contaminant to mechanical abrasion against a component of the filter system, ionization with material formed as a result of interaction of UV-radiation with an element of the filter system, and direct irradiation of the contaminant with UV-radiation.

17 Claims, 8 Drawing Sheets

| Item | Description |
|---|---|
| 101 | Body Housing |
| 102 | UV-C LED Mount |
| 103 | Collector Bracket |
| 104 | Collector Pin |
| 105 | Collector Tube |
| 106 | Deflector Tube |
| 107 | Housing Pin |
| 108 | Housing Spacer |
| 109 | UV-C LED Board |
| 110 | Led Board Connecto |
| 111 | Filler |
| 112 | Foil Tape |

| Item | Description |
|---|---|
| 101 | Body Housing |
| 102 | UV-C LED Mount |
| 103 | Collector Bracket |
| 104 | Collector Pin |
| 105 | Collector Tube |
| 106 | Deflector Tube |
| 107 | Housing Pin |
| 108 | Housing Spacer |
| 109 | UV-C LED Board |
| 110 | Led Board Connecto |
| 111 | Filler |
| 112 | Foil Tape |

| ITEM | DESCRIPTION |
| --- | --- |
| 501 | CONTROL BOARD |
| 502 | MOTORIZED IMPELLER |
| 503 | INLET |
| 504 | ACOUSTICAL FOAM |
| 505 | UV-CASE |
| 506 | UV-CASE AIR GUIDE/LIGHT DAM |
| 507 | EXHAUST DEFLECTOR |
| 508 | COVER |
| 509 | STAGE 3 CONNECTION |
| 510 | STAGE 3 LIGHT |
| 511 | LIGHT PANEL |

FLUID-FLOW STERILIZATION ENGINE AND METHOD FOR USING THE SAME

CROSS-REFERENCE TO RELATED APPLICATIONS

This application is a divisional from the U.S. patent application Ser. No. 17/405,367 filed on Aug. 18, 2021 and now published as US 2022/0054697, which claims the benefit of and priority from the U.S. Provisional Patent Applications Nos. 63/067,239 filed on Aug. 18, 2020; 63/068,151 filed on Aug. 20, 2020; and 63/070,517 filed on Aug. 26, 2020. The disclosure of each of the above-identified patent applications is incorporated herein by reference.

TECHNICAL FIELD

The present invention relates to system and method configured to prevent the transmission of pathogens and viruses with the flow of fluid (such as liquid or air, for example) and, more particularly, to an UV-generating apparatus with a filter system judiciously designed to not only increase the amount of time during which the flow of fluid containing an organic contaminant (pathogen, virus) is irradiated with the UV light but also avoid the physical separation of the contaminant from the flow of fluid while, at the same time, additionally exposing the contaminant to chemical oxidation.

RELATED ART

Many specific health challenges exist in the world today, but two primary concerns overshadow the rest: the maintenance of pathogen-free air delivered in indoor spaces and maintenance of hygienic conditions to prevent the creation or distribution of germs and pathogens.

Providing centrally located broad-spectrum infection prevention in HVAC systems to the same level of infection prevention that is required at a local point of contamination (that is, at a particular location in a given indoor space) is economically unfeasible. In fact, most central based HVAC infection prevention devices leave many indoor areas completely untreated due to the device location along with its physical limitations and cost.

It is also recognized that existing systems configured to sterilize the air flow take too long a time to prevent the infection of inner spaces, and such systems are powered by high-voltage AC electronics that are known to be often unreliable and costly. The primary limiting factor in existing systems is that the infection-prevention apparatus is usually centrally, located which is too far from the local point of contamination.

SUMMARY OF THE INVENTION

An embodiment of the present invention provides a filter apparatus configured to filter a fluid. Such apparatus includes a first filter system that contains three structural layers. A first structural layer is defined by a first array of first rods that extend substantially along a first axis (here, immediately neighboring first are separated from one another by first gaps). The second structural layer is defined by a second array of second rods that extend substantially along the first axis, and that are substantially staggered with respect to the first rods when viewed along a normal to the first structural layer to cause impact between a component of the fluid passing through the first structural layer towards the second structural layer and the second array prior to transmitting said fluid through the second structural layer. The third structural layer is separated from the first structural layer by the second structural layer, and is being dimensioned to reduce pressure of a flow of the fluid, which has passed through the first structural layer and then through the second structural layer in a direction of the normal, upon passing of the fluid through the third structural layer. The filter apparatus additionally includes a source of radiation configured to generate radiation at a working wavelength in a chamber of the filter system, the chamber being separated from the first structural layer by the second and third structural layers. In a specific case, the filter apparatus includes a second filter system separated from the first filter system by the chamber. (The second filter system includes a fourth structural layer substantially identical to the third structural layer, a fifth structural layer substantially identical to the second structural layer, and a sixth structural layer substantially identical to the first structural layer. The fourth structural layer is facing the chamber and the sixth structural layer is separated from the fourth structural layer by the fifth structural layer.)

Embodiments of the invention additionally provide a method for filtering a fluid. Such method includes the operational steps that are performed with the use of a first filter system that includes a first structural layer, a second structural layer, and a third structural layer as described above, and such operational steps are: (a) passing the fluid along a first direction of flow of the fluid through the first structural layer that is defined by a first array of first rods, the first rods extending substantially along a first axis, immediately neighboring first rods being separated from one another by first gaps; (b) receiving the flow of the fluid through the first structural layer at the second structural layer defined by a second array of second rods that extend substantially along the first axis and that are substantially staggered with respect to the first rods, and transmitting the flow of the fluid through the second structural layer; and (c) reducing pressure of the flow of the fluid by passing the flow through a third structural layer spatially separated from the second structural layer in the first direction. The method further includes the step of irradiating the second array with radiation having a working wavelength and arriving at the third structural layer in a second direction. In at least one implementation, the method may satisfy the following conditions: the step of passing includes passing the flow between the first rods made of a first material that is substantially opaque to the radiation, and/or the step of receiving includes impinging the flow on the second rods made of a second material that is substantially transparent to the radiation. Alternatively or in addition, and in at least one implementation, the first structural layer may have a first cross-sectional area in a first plane substantially transverse to the first direction, and/or the second structural layer may have a second cross-sectional area in a second plane that is parallel to the first plane; and/or the step of reducing of pressure is achieved by passing the flow through the third structural layer with a third cross-sectional area, formed in a third plane that is parallel to the first plane (here, the third cross-sectional area being smaller than at least one of the first and second cross-sectional areas). The third cross-sectional area may be limited on opposing sides by respective ridges, each ridge defined by respectively corresponding two surfaces which form a dihedral angle and at least one of which reflects said radiation away from the second structural layer during the step of irradiating. In substantially every implementation, the method may include at least one of the following steps: transmitting the flow from the third structural layer through a spatial gap separating the first filter system to a second filter system that is structured substantially identically to the first filter system, and additionally filtering said fluid by passing the fluid through the second filter system while preventing a backpressure of the fluid onto the first filter system to exceed 15 Pa (Pascal units). Alternatively or in addition, and in substantially every implementation, the method may include ionizing a material component of the flow a least in part by interacting the radiation with a first component of a first rod of the first array and/or by interacting the radiation with a second component of a second rod of the second array. (In this case, the action of causing may include a free radical molecule, generated by irradiating a first coating layer of the first rod and/or a second coating layer of the second rod, to the material component.) Alternatively or in addition, at least one of the following conditions may be satisfied: a second rod of the second array and/or a first rod of the first array is dimensioned as a tube; and/or such tube contains a supporting material rod in a hollow thereof.

BRIEF DESCRIPTION OF THE DRAWINGS

The invention will be more fully understood by referring to the following Detailed Description of Specific Embodiments in conjunction with the Drawings, of which.

Figure 1:
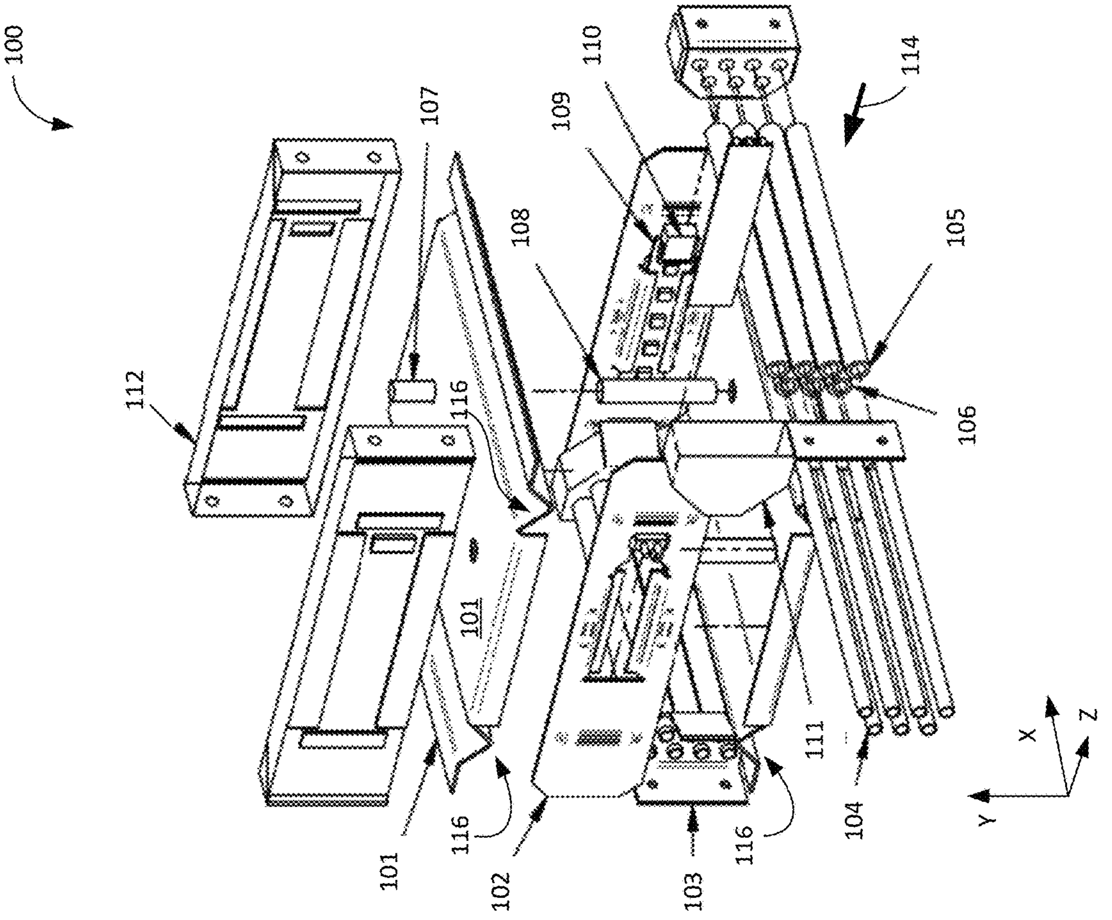
FIG. 1 is a schematic of an embodiment of the apparatus of the invention, in exploded view.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

References to the target organic contaminants of the flow of fluid of interest (such as air or liquid, for example, water) will be made by interchangeably referencing either a pathogen, or a virus, or simply a contaminant.

The problems of related art—that manifest in high-operational costs of pathogen deactivation (which includes high-levels of UV radiation and/or flux densities, required to adequately irradiate the pathogens in the flow of fluid, and/or residues of live pathogen preserved in portions of the conventional filter/sterilization systems as a result of mechanical separation of the pathogen from the flow of fluid)—are solved by employing a filter system judiciously designed to include at least three structural layers providing for the combination of Bernulli and Venturi effects (as far as the flow of fluid passing through such layers is concerned) while, at the same time, exposing the contaminant to mechanical impact and ionization to weaken the outer layers thereof. The optical and/or mechanical and/or geometrical properties of the components of these three structural layers differ from one another in that the components of the first layer and those of the second layer are spatially staggered with respect to one another; that the components of the first layer remain substantially opaque to radiation used to irradiate the flow of fluid along a direction that is substantially to the direction of propagation of the flow through the filter system; and that the components of the second layer, while being substantially optically transparent to such radiation, are geometrically configured to produce multiple reflections of the radiation in the second layer such as to increase contaminant-irradiation time.

For the purposes of this disclosure and the attached claims, the term filter (or, more generally, filter system) and related terms (such as filtering, for example) are defined to designate an article of manufacture through which fluid is passed to deactivate, render substantially inoperative, and/or reduce the content of a living organism or infection agent in such fluid, as well as the process of operation of such article of manufacture. To this end, a substance or structure configured to separate out matter in suspension is not a filter for the purposes of the present disclosure; neither is an optical or acoustic or electrical component configured to minimize waves or oscillations at certain frequencies, for example. A staggered or staggering spatial arrangement is the arrangement in which the items of interest are placed on or as if on alternating sides of a center line; set in a zigzag row or rows. An example of the staggered arrangement is the arrangement of, for example, black squares of a chess board.

To this end, FIG. 1 provides a schematic illustration, in exploded view, of a specific example 100 of a fluid-sterilization apparatus configured according to the idea of the invention and the Table summarizing the description of at least some of the elements of the embodiment 100. A person of ordinary skill in the art will readily appreciate that inside the housing structure or chamber (which is assembled from the structural elements such as elements 101 (which are the upper and lower plates or top and bottom of the chamber), 102, 103, 108, 111, 112, the embodiment of the invention includes a filter apparatus or system that includes generally the first, second, and third structural layers sequentially encountered by a flow of fluid 114 entering the fluid-sterilization apparatus 100 substantially transversely to the array of the elements 105, in a direction indicated by the arrow 114. Aggregately, such first, second, and third structural elements form the first filter subsystem (disposed on one side of the chamber that is otherwise limited by upper and lower plates and auxiliary sidewalls, and within which there is a least one radiative source 109 configured to generate radiation at a wavelength judiciously chosen to cause at least a disruption of living conditions of the pathogen contaminant contained in the fluid being sterilized). The second filter subsystem—which in at least one case can be structured substantially similarly to the first filter subsystem—may be disposed opposite the first filter subsystem such as to be separated from it by the chamber of the overall apparatus 100. When present, the second filter subsystem not only operates in the same fashion as the first filter subsystem (as is described below in details), but also provides the outward path for the flow of fluid that has entered the apparatus 100 along the arrow 114.

These three structural layers will now be described in reference to not only FIG. 1 but also FIG. 2 (showing the embodiment 100 is an assembled view, with a partial cut-out) and FIG. 3 that illustrates schematically, in a side view, a specific but not-limiting variation 300 of the example 100.

Figure 3:
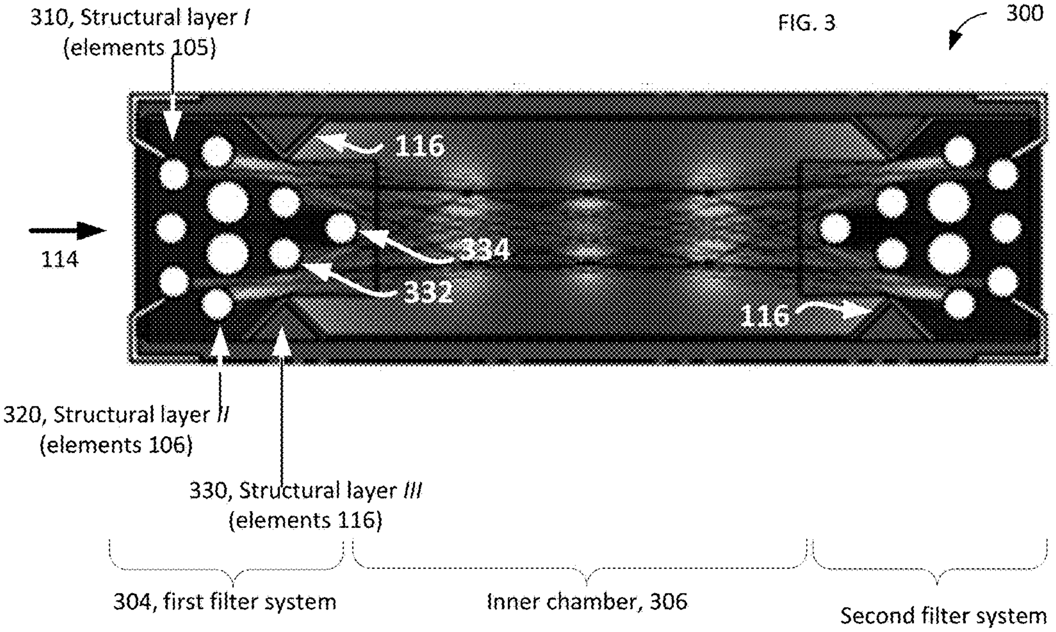
FIG. 3 is a simplified side-view of an embodiment similar to that of FIG. 2 with indication of distribution of light field inside the chamber of the embodiment and towards the first and second filter systems limiting such chamber.

The first filter system 304 includes a combination of the components of the first structural layer (structural layer I, or 310, as marked in FIG. 3, which includes at least the array of the rod-like elements 105 referred to in FIG. 1 as collector tubes, which are generally non-transparent to the radiation produced by the source 109) and the second structural layer (structural layer II, or 320, as marked in the example of FIG. 3, which includes at least the array of the rod-like elements 106 referred to in FIG. 1 as deflector tubes, which are generally transparent to the radiation produced by the source 109 and are structured to multiply reflect such radiation by and among the surfaces of the rods 106 such as to increase the degree of interaction between the flow of fluid 114 passing through the structural layer II and the radiation at hand). The rods of the first structural layer 310 and the rods of the second structural layer 320 are staggered with each other in that the flow of fluid 114 passing between and around the rods 105 immediately and head-up impinges only the rods 106 of the second structural layer, thereby creating mechanical impact between the contaminant component contained in the fluid flow (such as a pathogen or virus) and the surfaces of not only the rods 105 but the rods 106 as well.

Figure 2:
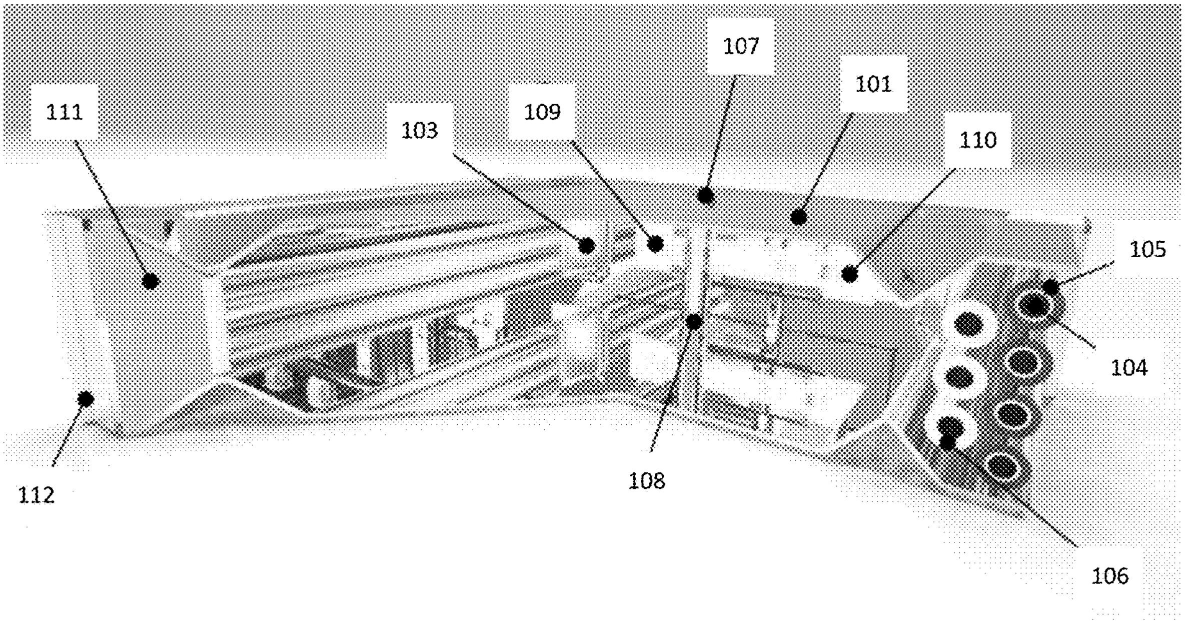
FIG. 2 is a partially-cut-out perspective view of the assembled apparatus of FIG. 1.

Structured as is schematically shown in the examples 100, 300 of FIGS. 1, 2, and 3, the rods 105 are dimensioned as tubular elements of, for example, aluminum that extend alongside the chamber 306 of the apparatus and can be internally supported by the stems or pins 104 passing through the hollows of the rod 105 when the apparatus 100, 300 is being assembled. Structured as is schematically shown in the examples 100, 300, the rods 106 of the array of the second structural layer 320 are made of optically-transparent (at the working wavelength) material such as, for example, soda-lime glass and in at least one implementation are dimensioned as substantially cylindrical. (A person of ordinary skill in the art understands that, although in a preferred embodiment the cylindrical shape of the rods is discussed, generally rods 105, 106 may have a differently shaped outer surface.) In this example, a cylinder is used as a shape for the outer surface of the rods of the embodiment for at least two reasons: this shape is readily available and provides a low drag coefficient (thereby allowing the flow of fluid to pass through the system without substantially impeding the flow). The drag coefficient is known to be a figure of merit used in aerodynamics to model all of the complex dependencies of drag on shape, inclination, and some flow conditions. The drag coefficient Cd is assessed based on the value of the drag D normalized by density r and reference area A times one half of the squared value of velocity V of the flow (see, for example, Shape Effects on Drag on nasa.gov website)):

$$C_d=D/(0.5rV^2AZ)$$

Figure 4A:
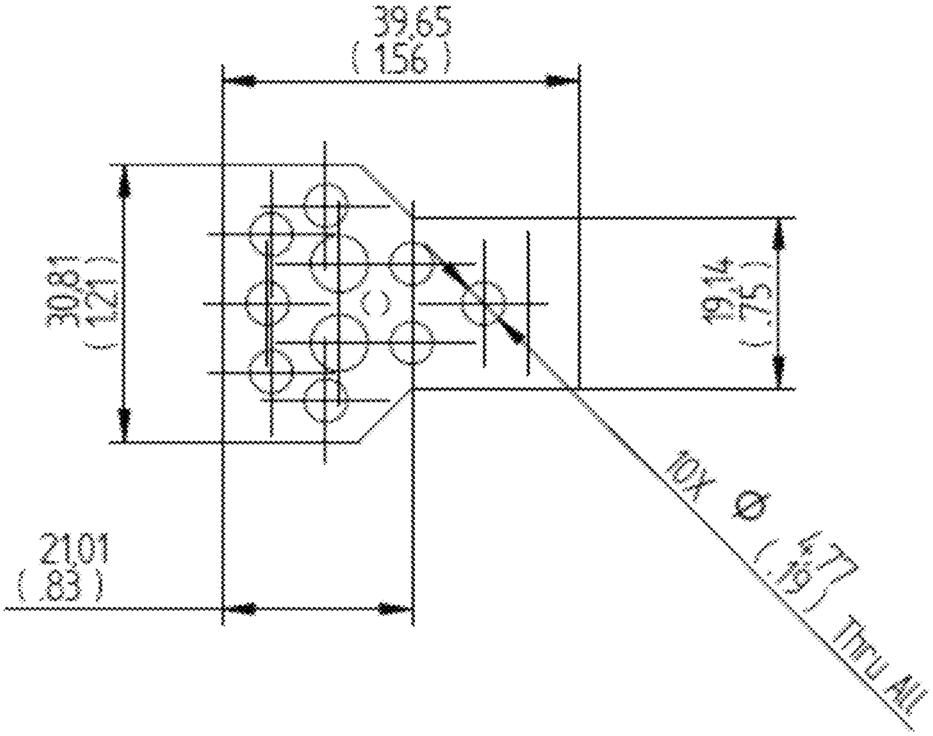
FIGS. 4A, 4B, 4C, 4D, 4E, 4F, and 4G present components of the housing of the apparatus, thereby providing an example of geometrical configuration of an embodiment of the invention.
Figure 4B:
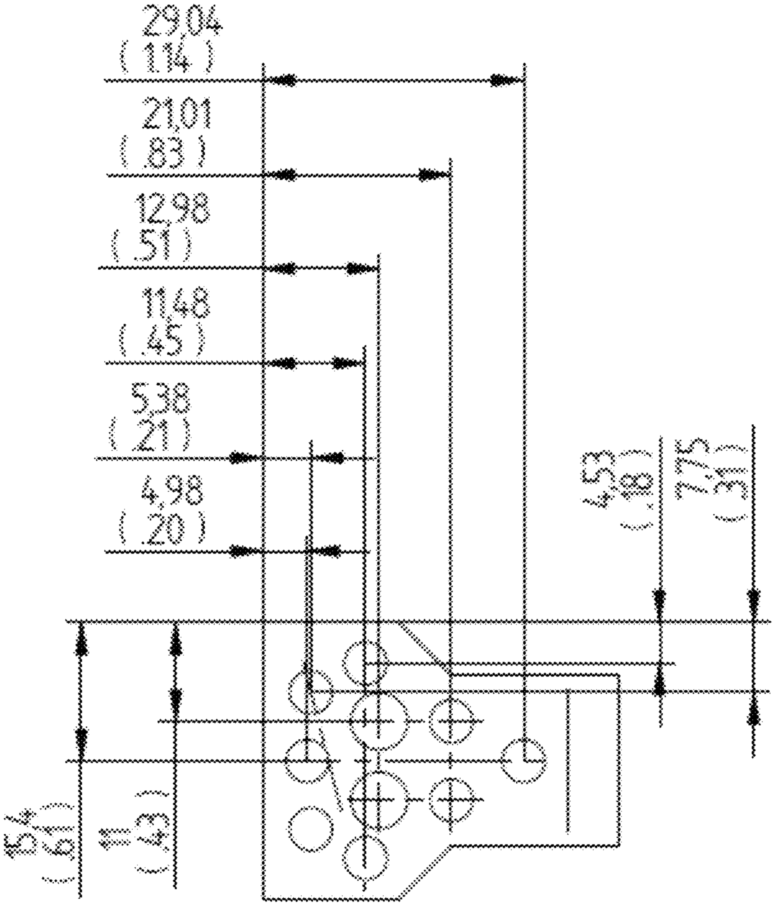
Figure 4D:
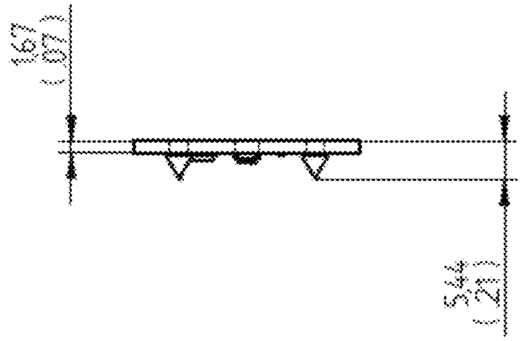
Figure 4C:
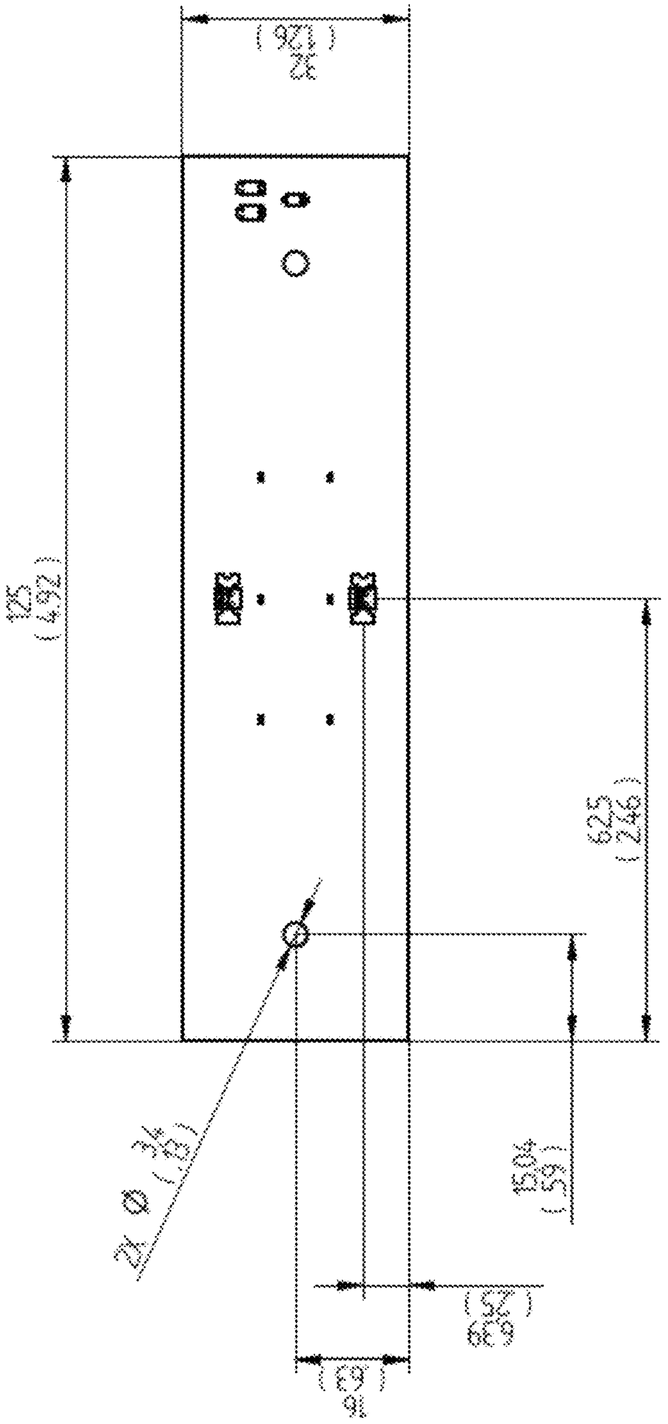
Figure 4F:
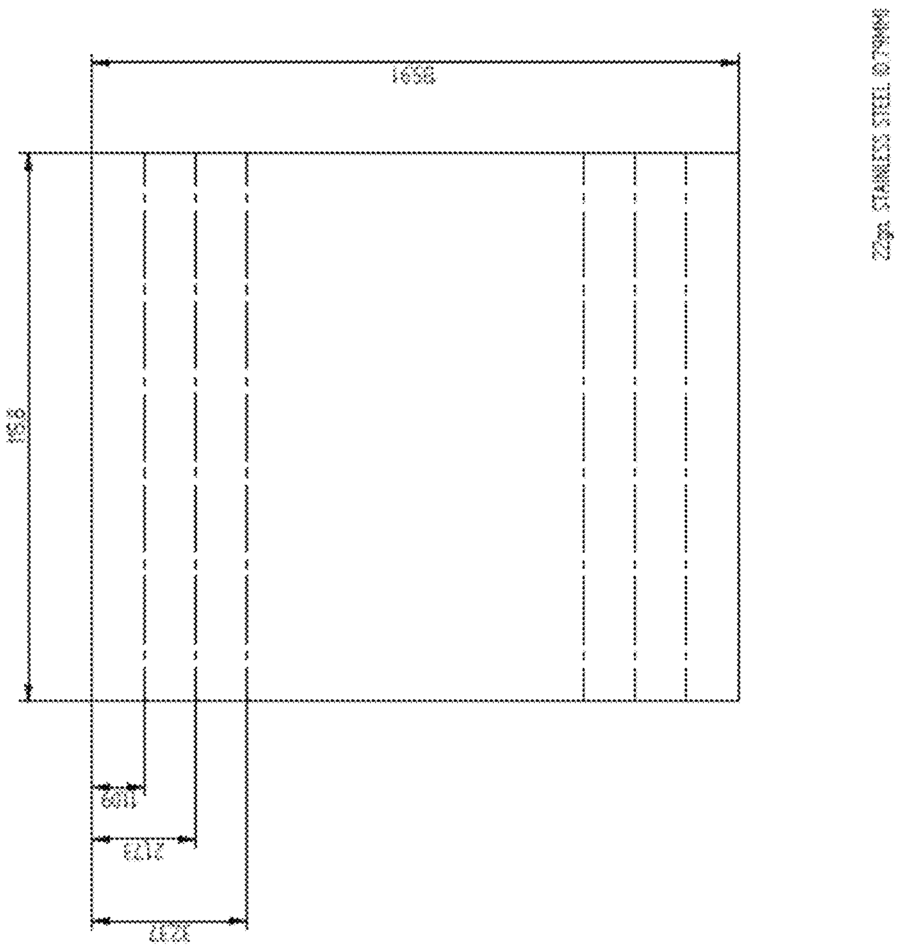

In at least one case, glass tubes may also be optionally supported from inside by the corresponding axial stems or pins 104. One non-limiting example of geometry of the first filter system 304 can be unambiguously derived from illustrated in FIGS. 4A, 4B, for example. Generally, however, the rods 105, 106 can be configured as solid rods of substantially arbitrary cross-sectional shape, for example a cylindrical cross-shape or a polygonal cross-shape. It is understood that the number of rods in the array of rods of the first structural layer and the number of rods in the array of rods of the second structural layer may differ, as long as the staggered arrangement among such rods is substantially maintained.

The first filter system 304 additionally includes a third structural layer (marked in the example of FIG. 3 as structural layer III or 330), which is configured to reduce the pressure in the flow of fluid propagating through such third layer 300 as compared to the pressure established by the flow while propagating through at least one of the layers 310 and 320. As shown, the third structural layer 310 is bound from two sides (on top and on the bottom) with structural ribs or ridges which limit the vertical extent of the layer to extent that is smaller than the vertical extent of at least one of the structural layer 310 and the structural layer 320. As shown in the specific example of FIGS. 1, 2, and 3, the limiting ribs or ridges 116 are formed by the combination of two material surfaces of the top and bottom plates 101 that form a dihedral angle therebetween. (While in these examples the ribs 116 are shown to have a somewhat triangularly-pyramidal shape, it is understood that generally ribs, ridges, or otherwise shaped inward protrusions into the chamber from the surfaces of the plates 101 can be used to limit the vertical extent of the third structural layer of the first and/or second filter sub-system. In one non-limiting example, the inward protrusions may have a surface conforming to a surface of a sphere.)

The specific example of layer 330 of FIG. 3 additionally illustrates the presence of at least one optional rod 332 that may be disposed parallel to the extension of the rib 116 (which corresponds to the axis X of FIG. 1), to cause the Bernoulli effect upon the propagation of the fluid through the third structural layer. Furthermore, the specific example of FIG. 3 additionally illustrates that a given embodiment of the filter apparatus of the invention may optionally contain a centering rod or tube 334, the presence of which at least includes the degree of vorticity of the fluid flow upon the passage of the third structural layer, thereby additionally increasing the dwell time (as mentioned in reference to FIG. 6).

In at least one implementation, the outer surface of at least some of the rods 105, 106 is coated with a film judiciously configured to be a hard metal oxide film and/or to initiate a chemical reaction with the fluid 114 when irradiate with the radiation produced by the source(s) 109 (at or around, for example, 265 nm) such as to generate a molecule that, when attached to the pathogen component of the fluid 114, ionizes (oxidizes) such a component, thereby additionally detrimentally harming the pathogen. To this end, in at least one case all rods 105, 106 may be coated with a layer of anatase $TiO_2$ (from about 40 nm to preferably about 1 mil thick) to create a chemical reaction when exposed to UV rays that creates a safe free molecule Hydroxyl Radical (OH): ($H_2O_2$+UV=2 OH−), unlike ozone $O_3$, that attaches to pathogens which weakens and accelerates the destruction of their outer membranes by oxidation. The $TIO_2$ is not used up in the process of such UV-photocatalysis, so the process can continue to breakdown organic molecules over-and-over again. Depending on the specific implementation, the concentration of the $TiO_2$ can be customized to obtain at least partially optically transparent film.

Figure 4E:
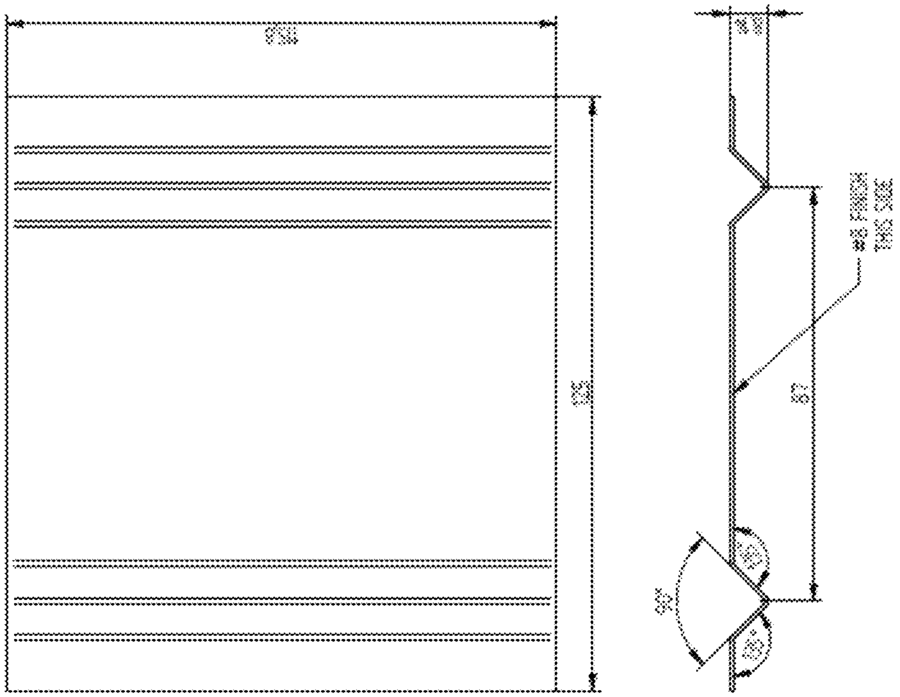
Figure 4G:
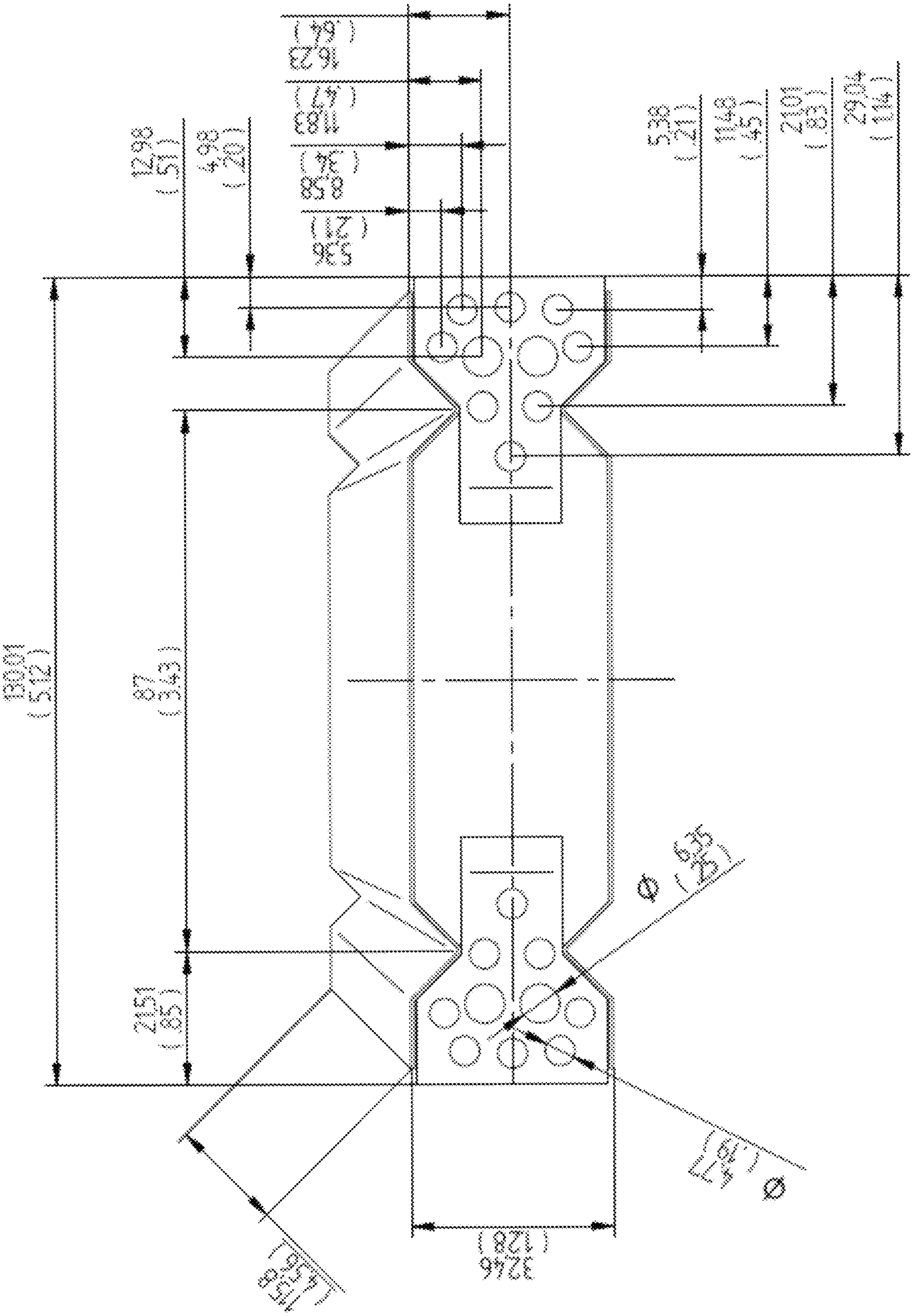

A person of skill in the art will readily understand one non-limiting example of geometry of the embodiment of the invention from the illustrations of FIGS. 4A through 4G. Here, unless otherwise specified, dimensions are in millimeters, values of angles are specified to within +/−1 degree. It is appreciated, that when the ribs 116 are formatted as inverse V-groove (as shown in FIGS. 3, 4E for example), the facets of such ribs provide additional effect of reflecting the UV radiation from the sources 109 in the inner chamber 306 and form a light-dam to cause the light energy to hit rods 106 located outside the chamber 306 which, in turn, generate multiple reflections of the radiation at and among the surfaces of the rods 106, thereby substantially increasing the UV radiant flux interacting with the flow of fluid 114 passing through the filter system 304 on its way to the chamber 306. It is appreciated that the combination of multiple reflections of the radiation produced insider the inner chamber 306 at the array of rods 106 and the substantially non-transparent nature of the array of rods 105 substantially blocks the UV light from penetrating through the filter system 304 outwards (from the chamber 306 to the ambient environment surrounding the embodiment 100, 300). In one non-limiting example, when the geometry of the embodiment was substantially the same as that depicted in FIGS. 4A through 4G, and when the rods 105 were fabricated from Aluminum, the rods 106 were fabricated from the soda-lime glass 104 was 135 cubic feet per minute (cfm) and the coating of titania covering the rods 105, 106 was chosen to be ~1 mil, and when the UV sources 109 inside the chamber were configured to generate 0.12 Watts of UV light within the spectral range from about 255 nm and about 280 nm, the percentage of UV light that has penetrated through the first filter sub-system 304 outwardly (against the arrow 114) was substantially zero (0) lux as measured using an Omega HHLM112SD Light meter logger and, generally, below the level of 0.01 lux. In practical terms, therefore, the first filter system (and, accordingly, the second filter system-see FIG. 3) substantially block the UV radiation from penetrating from the chamber of an embodiment through the first array to the ambient environment.

In a substantially similarly structure system, and with the flow of air 114 delivering about 2.25 cfm of air into the chamber per second, the dwell time was about 0.12 s while the back pressure of air (applied to the first filter system 304 in a direction opposite to that indicated by the arrow 114) did not exceed 15 Pa. These operational parameters are advantageously distinguishing the operation of the embodiment of the invention from those known in related art, which are subject to at least 25 Pa to 62.3 Pa of backpressure.

Referring again to the schematic of the example 100 of FIG. 1, components 101 and 102 are preferably made of highly polished UV-reflecting metals (for example, steel plates) in order to deflect and keep UV light concentrated and contained inside the UV-CASE. Items 103 through 106 are assembled with the use of mechanical deformation of the ends of item 1044, Collector Pin, on the outside of item 103. The component 103 (Collector Bracket) is preferably shaped in a way as to guide the flow of fluid (air, for example) toward items 105, Collector Tube, and item 106, Deflector Tube, in order to minimize air restriction. The overall assembly creates a cage (chamber) for UV light by utilizing UV reflective materials coated with antimicrobial coatings to contain scattered Light inside the apparatus 100 and kill or harm microorganisms entering or exiting the unit on the inside layer, and UV absorbing materials on the outside with an antimicrobial finish to prevent UV light from exiting the unit. The Housing is connected using components 108, housing spacer, and 107, housing pin, by distorting the ends of the housing pin using mechanical force. The housing spacers can be made of a rounded and smoothed UV-absorbing material to minimize scattering of UV light due to obstructing the UV-C LED emitters and air flowing through the UV-CASE assembly. The component 109 is a UV-C LED rigid board module configured to generate UV-C light within the spectral range from about 222 nm to about 275 nm inside the chamber of the apparatus 100. The component 110 provides power to the UV-C LED module and is made of materials that can withstand constant UV-C exposure over long periods of time. The element 111 is a filler material configured to prevent fluid 114 (air) from escaping the unit without flowing past rods 105, 106, and is made from an UV-stable material such as melamine foam, for example, so it can be oversized to maximize sealing potential and maintain said seal after prolonged exposure to UV radiation. The component 112 is used to cover all seams and openings from the outside of the unit to further prevent air and UV light from escaping from the unit from anywhere other than the desired entry and exhaust ports.

Figure 6:
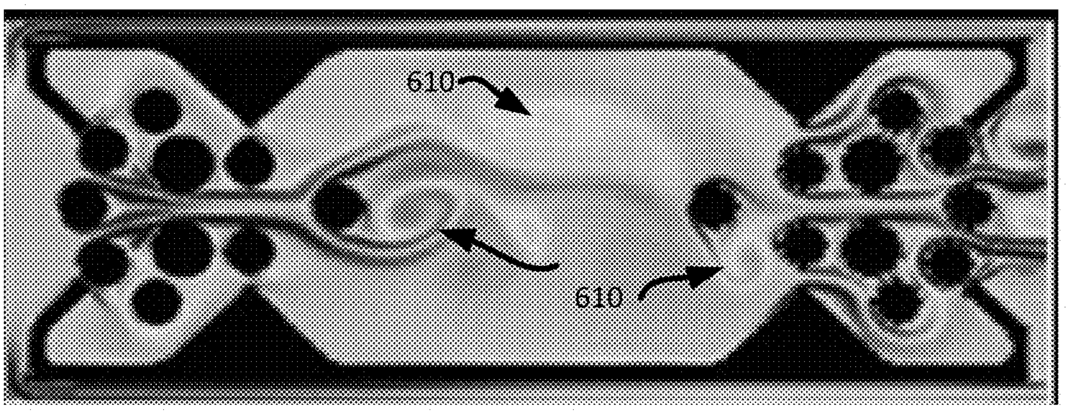
FIG. 6 schematically illustrates the formation of vortices in the flow of fluid, flowing at speeds corresponding to about 2.25 cfm through the chamber of the embodiment of the invention, which facilitates the about 10× increase of dwell time (>0.1 sec) of fluid in the embodiment as compared to that (~0.01 sec) in systems of related art.

It is appreciated, therefore, that embodiment of the invention provides the first infection-prevention measure implemented in the form of an array of specially coated metal cylindrical rods that act as a "shredder", which injures the protective outer membrane of pathogens as forced air accelerates through the body of the overall apparatus which increases the effectiveness of the specialized coatings, such as Micro ban and Invesil. The rods are strategically positioned to create turbulence and further disturb the air flow to increase the collision of pathogens in the field and create greater exposure when the pathogen enters the inner "light chamber" containing LEDs, this area includes an array of light emitting diodes (LED) producing light at a wavelength of about 222 nm, preferably at wavelengths exceeding 222 nm, and in at least one embodiment—at wavelengths within the spectra range from about 255 nm and 280 nm. (Notably, the use of such longer—wavelength regime of irradiation of the pathogen-contaminants is made possible due to dwell time, experienced by the flow of air upon transmission from the ambient environment to the inner chamber through the filter system of the apparatus of the invention, being increased from about 0.01 sec or so in apparatus of related art to more than 0.1 second in operation of the embodiment of the invention. In particular—as is schematically illustrated in FIG. 6, showing the results of the fluid flow distribution throughout the structural layers of the filter system and the chamber of the embodiment of the invention, the increased dwell time is partially due to the formation of vortices 610 in the flow of fluid not only between the first and second structural layers—as indicated in FIG. 6—but also upon the penetration of the flow through the three structural layers, in the chamber itself.)

Once the pathogen-containing flow of fluid (air, in one example) moves through the filter system, it encounters a second array of specially placed rods made of optically-transparent material such as soda lime glass (that are dimensioned to not only refract the UVC light rays preventing those rays from leaving the confines of the raceway or area that the engine is occupying, but that also act as a "light multiplier" increasing the spatial density of the scattered field in excess of the Navy MILL-SPEC of 225 μmols, which is a measurement of light intensity in at last one specific case.

The third structural layer encountered by the flow of fluid upon its transmission towards the inner chamber of the apparatus is judiciously structure to at least reduce the aperture A skilled artisan will readily appreciate that an embodiment of the invention is easily compatible with, for example, commercially available equipment such as HVAC units, air handlers, heat pumps, and diffusers. Specifically, an apparatus configured according to the idea of the invention is configured to sterilize pathogens at the local point of contamination (LPOC), in the space where people congregate (for example, in a particular room). Such apparatus is powered by low voltage DC current supplied from products like PoE servers that comply with IEEE 802.3bt (4PPoE) (Type 3) (Type 4), or midspan power injectors like the DESTINE® DC power server, and the use of the embodiment eliminates the need for additional main system HVAC duct work and high voltage AC power. Embodiments of the invention lend themselves to being included as an OEM component in existing products of third-party HVAC manufacturers.

In accordance with an example of embodiment, described with reference to FIGS. 1-4 and 6, a specific filter system has been discussed. While specific geometrical values and materials chosen for this embodiment are recited, it is to be understood that, within the scope of the invention, the values of all of parameters may vary over wide ranges to suit different applications. For example, in a related implementation, components 107 and 108 can be replaced by acrylic based adhesive that bonds the body housing plates to item 103; item 103 can be made with a UV stable material; components 109 and 102 cab be combined into one item; component 110 can be repositioned to the middle of the UV-C LED board utilizing a copper poke in a connector; component 11 can be changed to a dielectric to insulate the electronics and exposed traces of the UV-C LED board traces; components 104, 105, and 106 can be rearranged to further increase air flow, maximize purposed effects, and block direct UV light leakage from the chamber; while component 104 can be structured from a UV reflecting material and a mounting pin for the component 105; component 105 is soda lime glass, while component 106 can be made of an antimicrobial material.

Embodiments of the invention were implemented in a LPOC-sterilizing system of at least two varieties: a 2-prot sealed air-sterilizer appliance and a 4-port sealed air-sterilizer appliance.

Figure 5:
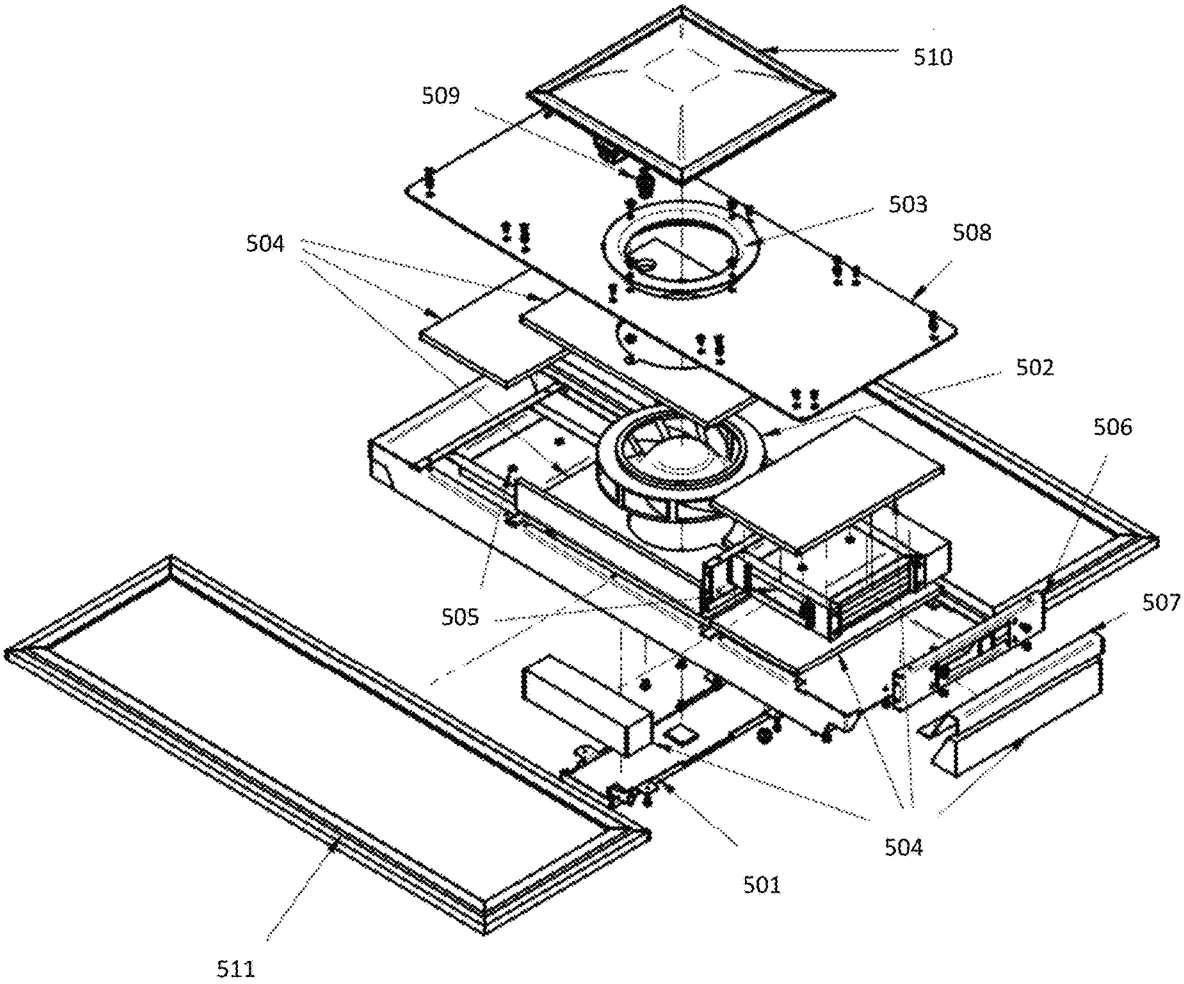
FIG. 5 is an exploded view of an embodiment configured as a 2-stage air-sterilization engine.

In the first case—and in reference to the schematic of FIG. 5, as discussed in U.S. Provisional Application No. 63/068,151—the 2-Port Sealed Air Sterilizer Appliance was designed to fit into a 2×2 T-grid drop ceiling or suspended or surface mounted to an open finished ceiling. The 2×2 Appliance included two filtering apparatus each configured according as embodiment 100 that flank a 135 cfm BLOC PWM fan/impeller connected to an intake duct centered on the bottom of such Appliance, which forced air up and through the flanking embodiment exhausted sterilized air back into the space below through an output duct at a rate of about 9.0 air changes per hour (ACH) combined for the two filtering apparatus. The 4-Port version Sealed Air Sterilizer Appliance contained eight filtering apparatus (such as that discussed in reference to FIGS. 1, 2, and 3; see for example U.S. Provisional Application No. 63/070,517), of which six filtering apparatus were connected to an existing forced HVAC output air duct by replacing the existing duct vent with a new duct adapter fabricated to size in field by HVAC contractor. The remaining two apparatus performed as a standalone 2-Port Sealed Air Sterilizer Appliance described above, except its part of a larger appliance designed for an indoor air sterilization application with higher ceilings and an existing forced air HVAC system. It is appreciated that unlike the 2-Port Sealed Air Sterilizer Appliance that only sterilizes air in spaces or rooms where people congregate, the 4-Port version of the Sealed Air Sterilizer Appliance is capable of and does sterilize both forced HVAC duct air before it enters a space and air in spaces or rooms where people congregate.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. The use of this term in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated may vary within a range defined by an experimental measurement error that is typical when using a measurement method accepted in the art for such purposes. For example, a reference to a vector or line or plane being substantially parallel to a reference line or plane is to be construed as such vector or line extending along a direction or axis that is the same as or very close to that of the reference line or plane (with angular deviations from the reference direction or axis that are considered to be practically typical in the art, for example between zero and fifteen degrees, more preferably between zero and ten degrees, even more preferably between zero and 5 degrees, and most preferably between zero and 2 degrees). For example, a term "substantially-rigid", when used in reference to a housing or structural element providing mechanical support for a contraption in question, generally identifies the structural element that rigidity of which is higher than that of the contraption that such structural element supports. As another example, the use of the term "substantially flat" in reference to the specified surface implies that such surface may possess a degree of non-flatness and/or roughness that is sized and expressed as commonly understood by a skilled artisan in the specific situation at hand. For example, the terms "approximately" and about", when used in reference to a numerical value, represent a range of plus or minus 20% with respect to the specified value, more preferably plus of, minus 10%, even more preferably plus or minus 5%, most preferably plus or minus 2%.

The invention as recited in claims appended to this disclosure is intended to be assessed in light of the disclosure as a whole.

What is claimed is:

1. A method for filtering a fluid with a filter apparatus, the method comprising:

with the use of a first filter system, of the filter apparatus, that includes a first structural layer, a second structural layer, and a third structural layer:

passing said fluid along a first direction of a flow of said fluid through the first structural layer that is defined by a first array of first rods, the first rods extending substantially along a first axis, wherein immediately neighboring first rods are separated from one another by first gaps;

receiving the flow of said fluid through the first structural layer at the second structural layer defined by a second array of second rods that extend substantially along the first axis and that are substantially staggered with respect to the first rods, and transmitting the flow of said fluid through the second structural layer;

reducing pressure of the flow of said fluid by passing the flow through a third structural layer spatially separated from the second structural layer in the first direction;

and irradiating the second array of second rods with radiation that has a working wavelength and that arrives at the third structural layer in a second direction.

2. A method according to claim 1, wherein said passing includes passing the flow between the first rods made of a first material that is substantially opaque to the radiation, and wherein said receiving includes impinging the flow on the second rods made of a second material that is substantially transparent to the radiation.

3. A method according to claim 1, wherein the first structural layer has a first cross-sectional area in a first plane that is substantially transverse to said first direction;

wherein the second structural layer has a second cross-sectional area in a second plane that is parallel to the first plane; and wherein the reducing pressure is achieved by passing the flow through the third structural layer with a third cross-sectional area, wherein the third cross-sectional area is formed in a third plane that is parallel to the first plane and is smaller than at least one of the first and second cross-sectional areas.

4. A method according to claim 3, wherein said third cross-sectional area is limited on each of opposing sides thereof by a respective ridge of two ridges, each of the two ridges defined by respectively-corresponding two surfaces that form a dihedral angle to reflect a portion of said radiation away from the second structural layer during said irradiating and to spatially concentrate the flow of said fluid upon passing from the second structural layer through the third structural layer.

5. A method according to claim 1, comprising:

transmitting the flow from the third structural layer through a spatial gap separating the first filter system from a second filter system that is structured substantially identically to the first filter system, and additionally filtering said fluid by passing the fluid through the second filter system while preventing a backpressure of the fluid onto the first filter system from exceeding 15 Pa.

6. A method according to claim 1, further comprising:

during said irradiating:

first multiply-reflecting said radiation within a first wall of a second rod of the second array, and second multiply-reflecting said radiation within a space at least partially limited by said first wall; and third multiply-reflecting said radiation between the first wall and a second wall of the second rod of the second array, to substantially block said radiation from penetrating through the first array.

7. A method according to claim 1, comprising:

substantially preventing said radiation from penetrating through the first filter system at least in part by:

multiply reflecting said radiation at elements of the second structural layer, and absorbing said radiation at the first structural layer and/or reflecting said radiation at the first structural layer towards the second structural layer.

8. A method according to claim 1, further comprising passing the fluid by a centering rod separated from the second structural layer by the third structural layer to increase a dwell time of the fluid above 0.1 second while preventing a backpressure of said fluid onto the first filter system from exceeding 15 Pa.

9. A method according to claim 1, further comprising causing ionization of a material component of the flow a least in part by interacting the radiation with a first component of a first rod of the first array and/or by interacting the radiation with a second component of a second rod of the second array.

10. A method according to claim 9, wherein said causing includes attaching a free radical molecule, generated by irradiating a first coating layer of the first rod and/or a second coating layer of the second rod, to said material component.

11. A method according to claim 1, wherein the passing said fluid through the third structural layer includes passing the flow of said fluid between upper and lower ribs and an auxiliary rod located between the upper and lower ribs to prevent a backpressure of said fluid onto the first filter system from exceeding 15 Pa, wherein the upper and lower ribs and the auxiliary rod are extending substantially parallel to the first axis.

12. A method according to claim 1, wherein (12*a*) a second rod of the second array and/or a first rod of the first array is dimensioned as a tube; and/or (12*b*) said tube contains a supporting material rod in a hollow thereof.

13. A method according to claim 1, further comprising:

transmitting the fluid through a chamber of the filter apparatus towards a second filter system of the apparatus separated from the first filter system by said chamber, the second filter system including a fourth structural layer substantially identical to the third structural layer, a fifth structural layer substantially identical to the second structural layer, and a sixth structural layer substantially identical to the first structural layer, wherein the fourth structural layer is facing the chamber and the sixth structural layer is separated from the fourth structural layer by the fifth structural layer.

14. A method according to claim 13, wherein at least one of the following conditions is satisfied:

the passing said fluid through the first structural layer includes passing the fluid through the first array of first rods that are disposed in a first non-planar surface, and the transmitting the flow of said fluid through the second structural layer includes transmitting the flow of said fluid through the second array of second rods that are disposed in a second non-planar surface to increase a dwell time of the fluid in the apparatus.

15. A method according to claim 13, further comprising irradiating the fluid with the radiation upon transmitting the fluid through the second filter system.

16. A method according to claim 1, further comprising: irradiating the fluid with said radiation upon propagation of the fluid through a chamber of the apparatus after the fluid has been transmitted through the first filter system.

17. A method according to claim 16, wherein at least one of the following conditions is satisfied:

the passing said fluid through the first structural layer includes passing the fluid through the first array of first rods that are disposed in a first non-planar surface, and the transmitting the flow of the fluid through the second structural layer includes transmitting the flow of the fluid through the second array of second rods that are disposed in a second non-planar surface to form vortices of the fluid is the chamber.

* * * * *